United States Patent [19]

Aileo et al.

[11] Patent Number: 4,905,322
[45] Date of Patent: Mar. 6, 1990

[54] ENERGY-ABSORBING EARCUP ASSEMBLY

[75] Inventors: Jackson A. Aileo, Carbondale; Richard J. Long, Lake Ariel, both of Pa.

[73] Assignee: Gentex Corporation, Carbondale, Pa.

[21] Appl. No.: 182,851

[22] Filed: Apr. 18, 1988

[51] Int. Cl.⁴ .............................................. A41D 21/00
[52] U.S. Cl. .......................................... 2/209; 2/411; 2/412; 2/423; 181/129
[58] Field of Search ................... 2/209, 6, 423, 411, 2/412, 10; 181/129; 381/158

[56] References Cited

U.S. PATENT DOCUMENTS

| | | | |
|---|---|---|---|
| 3,286,275 | 11/1966 | Marchello | 2/411 |
| 3,447,163 | 6/1969 | Bothwell et al. | 2/412 |
| 3,470,564 | 10/1969 | Aileo | 2/209 |
| 3,535,710 | 10/1970 | Aileo | 2/209 |
| 3,786,519 | 1/1974 | Aileo | 2/209 X |
| 3,815,155 | 6/1974 | Davison | 2/209 |
| 4,471,496 | 9/1984 | Gardner | 2/423 X |
| 4,551,861 | 11/1985 | Marchello | 2/209 X |
| 4,674,134 | 6/1987 | Lundin | 2/209 |
| 4,748,694 | 6/1988 | Aileo | 2/209 X |

Primary Examiner—Peter Nerbun
Attorney, Agent, or Firm—Shenier & O'Connor

[57] ABSTRACT

An energy-absorbing sound-attenuating earcup comprises a rigid shell of an ABS terpolymer that is about 0.090 inch thick so as to crush upon impact at an applied force less than that required to crush the skull of the wearer. The shell has an inner coating of a sound-deadening rubber material to compensate for the reduced sound-attenuating capability of the thinner-than-normal shell. Spaced flanges defining a peripheral channel for receiving a cord of a helmet suspension are formed as staggered series of tabs rather than as circumferentially continuous members to facilitate crushing of the shell upon impact. Resilient earseals disposed between the shells and the wearer's ears comprise first thicknesses of standard polyurethane foam and second thicknesses of slow-recovery polyurethane foam to provide additional impact absorption while permitting the earseals to conform to the wearer's head in cold weather when the helmet is first put on. The earcup may alternatively be releasably secured to the helmet by means of mating hook and loop fastener strips rather than being secured through the staggered tabs.

24 Claims, 3 Drawing Sheets

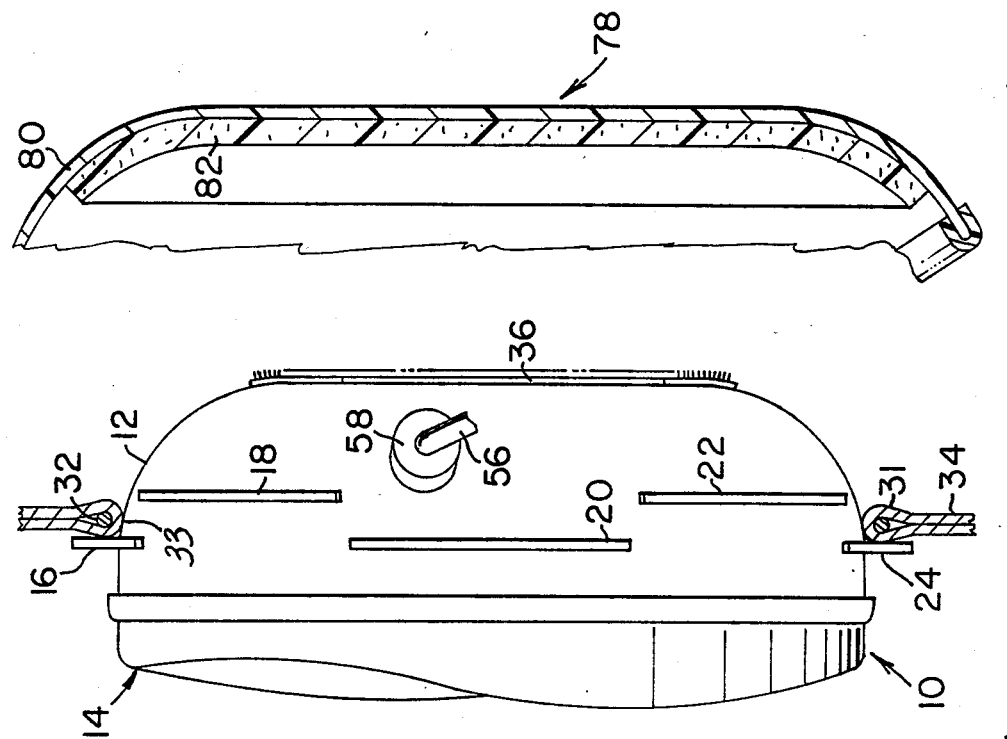
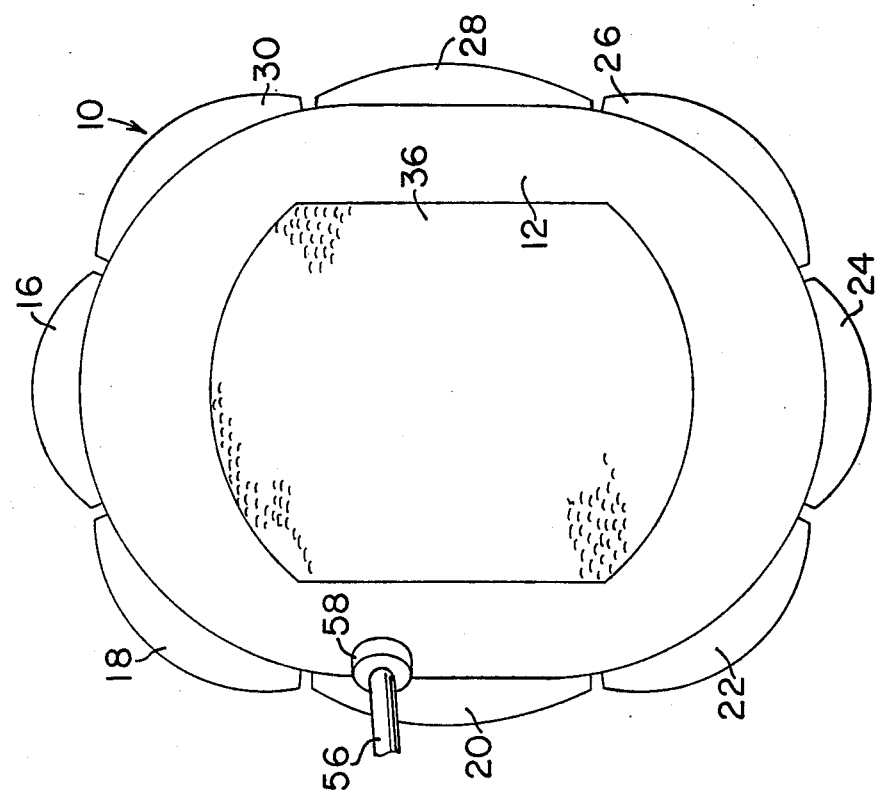
FIG. 5
FIG. 4

ENERGY-ABSORBING EARCUP ASSEMBLY

FIELD OF THE INVENTION

This invention relates to an energy-absorbing sound-attenuating earcup assembly for use in a protective helmet or the like, as well as to a protective helmet including such an assembly and to a compliant ear seal for use in such an assembly.

BACKGROUND OF THE INVENTION

Earcup assemblies for attenuating ambient sound in noisy environments, such as in or around military helicopters or other aircraft, are known in the art. Such assemblies are shown, for example, in U.S. Pat. Nos. 3,190,973, 3,470,564, 3,875,592 and 3,943,572, issued to applicant Jackson A. Aileo and owned by the assignee herein. As shown in the first patent identified above, the earcups of such assemblies may house earphones to allow communication or monitoring of the ambient sound. Generally in such assemblies the earcup shells, which comprise a rigid plastic, are about a quarter-inch thick to provide the necessary sound attenuation. As will be apparent from the above description, not only are such assemblies heavy, and thus uncomfortable after extended use, but the rigid plastic shell transmits lateral impact forces, such as might be sustained if the wearer falls against a hard object, almost without attenuation.

SUMMARY OF THE INVENTION

One of the objects of our invention is to provide an earcup assembly which minimizes the transmission of impact forces to the head.

Another object of our invention is to provide an earcup assembly which satisfactorily attenuates ambient sounds.

A further object of our invention is to provide an earcup assembly which is relatively lightweight.

Still another object of our invention is to provide an earcup assembly which conforms to the contours of a wearer's head.

An additional object of our invention is to provide an earcup assembly which operates satisfactorily in cold weather.

A further object of our invention is to provide an earcup assembly which is compatible with existing helmets.

Other and further objects will be apparent from the following description.

In one aspect, our invention contemplates an earcup assembly comprising a rigid shell of such a thickness as to crush upon impact at an applied force less than that required to crush the skull of the wearer. By crushing upon impact, the shell absorbs much of the energy of the impact rather than simply transmitting it to the wearer's skull. Preferably, the earcup shell comprises a acrylonitrile-butadiene-styrene (ABS) terpolymer having a thickness of about 0.09 inch to provide the desired crushability. In accordance with another aspect of our invention, we provide the earcup shell with the desired sound-attenuating capability by coating its inner surface with a layer of sound-deadening material, preferably a flexible vinyl rubber coating of about 0.010–0.015 inch.

Another aspect of our invention contemplates an earcup-mounting means in which a channel extending circumferentially along the outer surface of the shell is formed by respective pluralities of circumferentially spaced, outwardly extending tabs defining the sides of the channel. The channel thus formed receives a cord carried by the helmet suspension to secure the earcup to the suspension and therefore the helmet. Forming the channel in this manner improves the crushability of the earcup over what it would have been if the channel had been formed with continuous circumferential flanges as in the prior art. Preferably, the tabs are rounded so as to be shorter at their ends, thereby avoiding sharp corners which might otherwise catch on parts of the helmet.

Still another aspect of our invention contemplates a resilient earseal comprising an energy-absorbing material for sealing the region between the earcup and the wearer's head. Preferably the energy-absorbing material comprises an annular layer of slow-recovery polyurethane foam. The inclusion of the slow-recovery foam layer contributes to the overall impact-absorbing capability of the earcup assembly as well as to its sound attenuation and conformability with th wearer's head. At the same time, the retention of the normal-recovery foam layer allows the earseal to conform to the wearer's head when the assembly is donned at temperatures below 40° F. and the slow-recovery layer is initially stiff.

BRIEF DESCRIPTION OF THE DRAWINGS

In the accompanying drawings to which reference is made in the instant specification and which are to be read in conjunction therewith and in which like reference characters are used to indicate like parts in the various views:

FIG. 4 is a right side elevation of the earcup assembly of FIG. 1 with the earseal and earcup flange removed.

FIG. 5 is a rear elevation of the earcup assembly of FIG. 1 with the earseal removed, showing one form of mounting in a helmet assembly.

DETAILED DESCRIPTION OF THE PREFERRED EMBODIMENT

Figure 3:
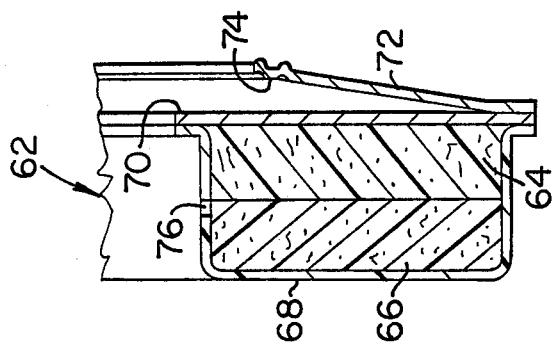
FIG. 3 is an enlarged fragmentary section of the earseal of the assembly of FIG. 1 as it appears when removed from the earcup.

FIGS. 1 to 5 show a right earcup assembly, indicated generally by the reference numeral 10, constructed according to our invention. The corresponding left earcup assembly is a mirror image of the right earcup assembly 10 and therefore has not been shown. Earcup assembly 10 includes a generally elliptical cup-shaped rigid shell 12 having an opening for receiving the ear of the wearer. Shell 12 preferably comprises a low-impact grade of plastic such as the acrylonitrile-butadiene-styrene (ABS) terpolymer sold under the trademark CYCOLAC. In accordance with one aspect of our invention, shell 12 has a thickness of 0.090 inch so as to crush upon impact at an applied force less than that required to crush the skull of the wearer. The disclosed shell 12, when used in combination with the helmet shell to be described, absorbs impact accelerations of to 175 times that of gravity at an impact velocity of 19.7 feet per second.

Figure 2:
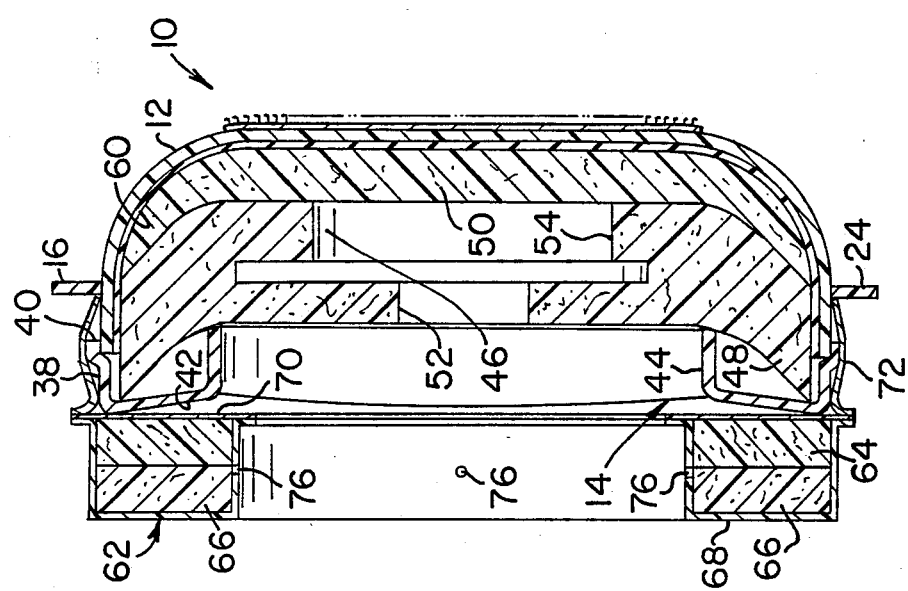
FIG. 2 is a section of the earcup assembly of FIG. 1, taken along line 2—2.

A flange indicated generally by the reference numeral 14 extends inwardly from the periphery of the shell 12 to define an opening for receiving the ear of the wearer. Preferably, flange 14 is formed from the same ABS terpolymer as shell 12, but somewhat thinner (e.g. 0.062 inch). Referring particularly to FIG. 2, flange 14 is formed with a peripheral portion 38 which is generally in register with the periphery of shell 12 and which is formed with a stepped shoulder portion 40 for receiving said periphery of the shell. Flange 14 also has a portion 42 extending inwardly away from peripheral portion 38 to define a smaller-circumference aperture for receiving the wearer's ear as well as to provide a support for the earseal to be described. Preferably the surface of portion 42 of flange 38 is contured in a manner complementary to that of the adjacent portion of the wearer's head as described in Aileo U.S. Pat. No. 3,875,592, the disclosure of which is incorporated herein by reference. Inwardly extending portion 42 of flange 38 in turn has a portion 44 extending in the direction of shell 12 and away from the wearer's ear. Flange 38 is secured to shell 12 by any suitable means such as a layer of cement (not shown) applied along the interface between shoulder 40 and the periphery of shell 12.

Earcup assembly 10 contains an earphone element 46 of any suitable type known to the art. Earphone element 46 fits within a complementary cutout 54 formed in an earphone pad 48 preferably comprising polyurethane foam. A circular aperture 52 formed in the ront of earphone pad 48 provides a direct acoustical coupling between earphone element 46 and the wearer's ear. A spacer pad 50 fills the interior of earcup shell 12 behind pad 48. Pads 48 and 50, shown in a compressed state in FIG. 2, are of uniform thickness when uncompressed and substantially of the shape of flange 14 as viewed in FIG. 1. In addition to locating earphone element 46, pads 48 and 50 enhance the impact-absorbing capability of assembly 10 by relieving the shell 12 of some of the impact force. Preferably pads 48 and 50 comprise high-porosity polyurethane foam to allow unrestricted transmission of sound from earphone element 46 to the wearer. Referring to FIGS. 4 and 5, a multiple-conductor cord 56 from earphone element 46 is passed through a grommet 58, received in an aperture (not shown) formed in shell 12, for coupling to an external communication system (not shown).

In accordance with our invention, shell 12 is provided on its inner surface with a coating 60 of sound-deadening material, preferably a heavy-duty flexible vinyl rubber coating available from Abbeon Cal, Inc. under the trademark PLASTIDIP. Preferably, two coats are applied by brush to form a layer 60 of 0.010–0.015 inch.

Figure 1:
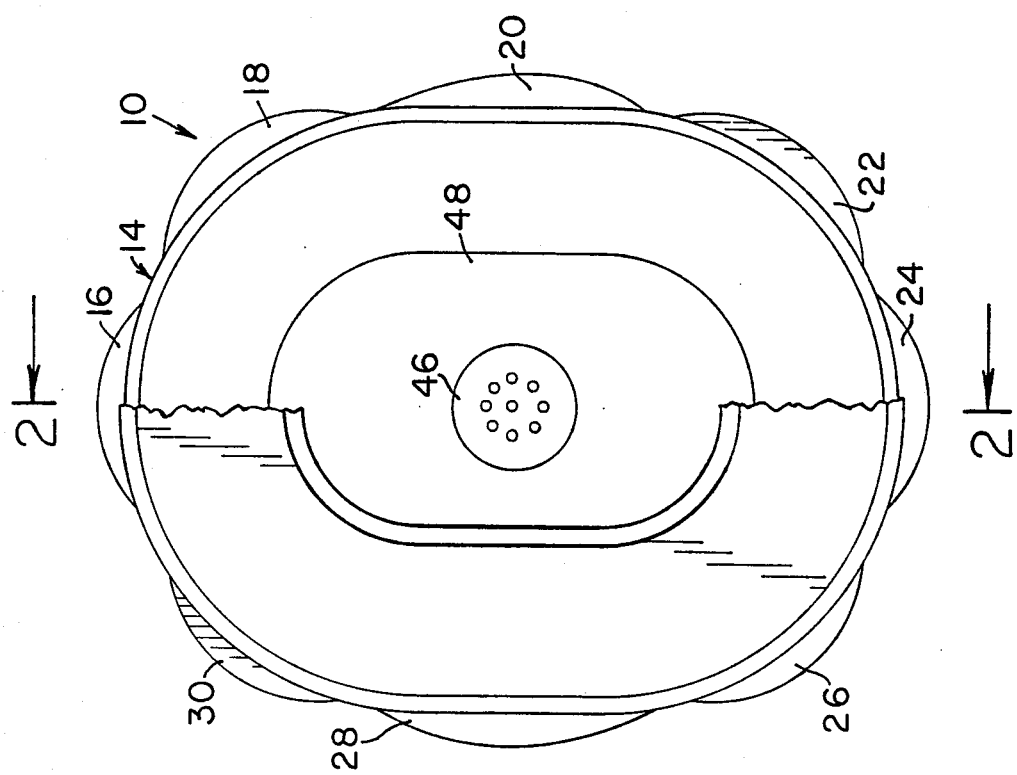
FIG. 1 is a left side elevation of a right earcup assembly constructed according to our invention, with parts broken away.

A plurality of tabs 16, 18, 20, 22, 24, 26, 28 and 30 extending outwardly from earcup shell 12 at circumferentially spaced locations about the periphery thereof define a circumferentially extending, outwardly opening channel for receiving a helmet suspension to be described. Tabs 16, 20, 24 and 28 are on the side of the channel adjacent to the wearer, while tabs 18, 22, 26 and 30 are on the side remote from the wearer. As shown in FIGS. 1 and 4, tabs 16, 20, 24 and 28 are offset from tabs 18, 22, 26 and 30 so as not to overlap about the periphery of earcup shell 12. Forming the sides of the channel as series of tabs in this manner rather than as circumferentially continuous flanges improves the crushability of the earcup 12, since the solid rings formed by such flanges would tend to resist crushing. Preferably, the tabs 16 to 30 are rounded so as to be shorter at their ends, as shown in FIGS. 1 and 4, so as not to present any sharp corners that might catch on other equipment. Tabs 16 to 30 are preferably about 0.062 inch thick and formed of the same ABS terpolymer as shell 12 and flange 14. Any suitable means such as cement (not shown) is used to secure tabs 16 to 30 on earcup shell 12.

Referring to FIG. 5, the channel formed by tabs 16 to 30 receives a fabric loop 31 surrounding an opening 33 in the side panel of a helmet suspension 34 such as shown, for example, in Aileo U.S. Pat. No. 3,470,564, the specification of which is incorporated herein by reference. A cord 32 disposed in the loop 31 is adapted to be tightened to hold the suspension 34 in engagement with the outer surface of earcup shell 12, as shown in the above-identifed patent.

Figure 6:
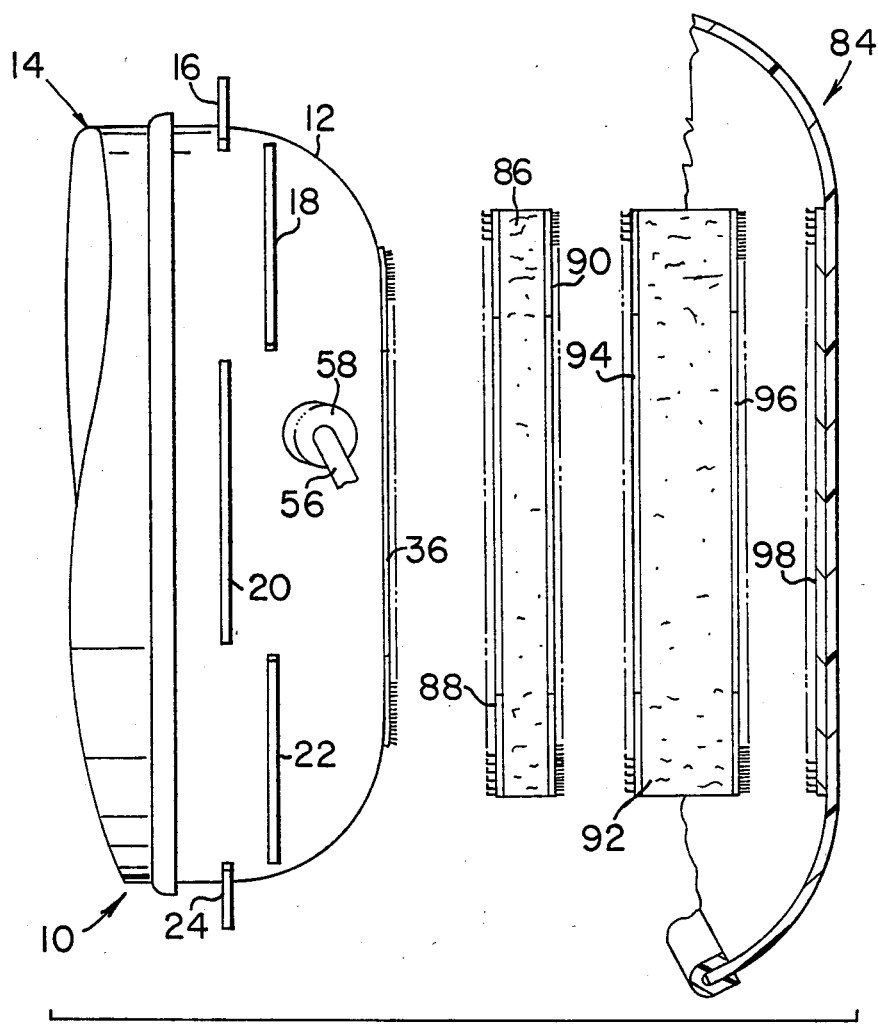
FIG. 6 is a rear elevation of the earcup assembly of FIG. 1 with the earseal removed, showing an alternative form of mounting in a helmet assembly.
Figure 7:
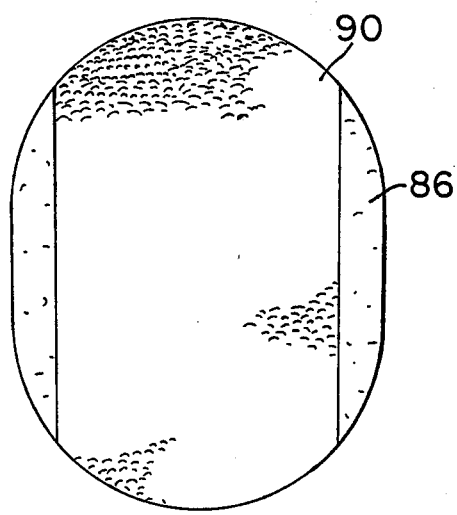
FIG. 7 is a right side elevation of one of the spacer pads of the mounting shown in FIG. 6.

Referring to FIGS. 2, 4 and 5, earcup shell 12 also carries a strip 36 of pile fastener material, such as that sold under the trademark VELCRO, to permit assembly 10 alternatively to be releasably secured to the mounting shown in FIGS. 6 and 7. Strip 36 may be omitted if earcup assembly 10 is only intended for mounting in helmet suspensions, such as the suspension 34 shown in FIG. 5 that engage tabs 16 to 30.

An earseal indicated generally by the reference character 62 resiliently seals the region between the wearer's head and earcup 12 and flange 14. Earseal 62, which has the elongated annular shape of flange 14, contains superimposed layers of polyurethane foam 64 and 66 each about 0.25 inch thick. Foam layers 64 and 66 are encased in an envelope formed from a base 70 and an outer cover 68 of 0.015-inch polyurethane film. Cover 68 is preformed in the shape shown in FIGS. 2 and 3 and is bonded to base 70 along the inner and outer peripheries thermally or ultrasonically. An annular lip 72 bonded in a similar manner to the outer periphery of base 70 on the other side from cover 68 is stretched over the periphery of flange 14 to retain earseal 62 on the earcup-flange subassembly. To facilitate assembly of the earseal 62 onto the flange 14, lip 72 is formed with a bead 74 on its inner surface as shown in FIG. 3. Perforations 76 formed at regular intervals about cover 68 vent the interior of earseal 62 to allow air to escape from the interior in response to external pressure. four 0.025-inch holes 76 are provided in the embodiment shown.

Layer 66, which is nearest the wearer's head, comprises standard polyurethane foam, while layer 64, which is nearest flange 14, comprises an energy-absorbing slow-recovery foam, such as the foam known as Temper Foam Type T-38. The inclusion of energy-absorbing layer 64 in earseal 62 contributes to the impact-absorbing capability of assembly 10 and, in addition, improves sound attenuation and the ability of earseal 62 to conform to the head at skin temepature. The layer of standard foam 66 is also included, however, since the energy-absorbing layer stiffens at temperatures below 40° F., and takes one or two minutes to soften in respone to body heat when the assembly 10 is first donned.

Helmet suspension 34 supports a helmet, indicated generally by the reference number 78, having a hard outer shell 80 extending over the earcup assembly 10 as shown in FIG. 5. Shell 80 may comprise any suitable material, such as 0.060-inch fiberglass or a 0.040- to 0.050-inch laminate of resin-impregnated layers of aramid cloth sold under the trademark KEVLAR. Shell 80 may optionally carry a polyurethane foam pad 82 opposite earcup assembly 10. Helmet shell 80 enhances the impact absorption of earcup assembly by distributing impact forces over a larger area of the earcup shell 12 than would be the case if the helmet shell were absent.

FIGS. 6 and 7 show an alternative earcup mounting using hook-and-loop fastener strips rather than the means shown in FIG. 5. More particularly, a modified helmet shell 84 carries on its inner surface a strip 98 of hook-type fastener material, such as that sold under the trademark VELCRO, that releasably adheres to the pile material of strip 36. Earcup 10 may be secured to fastener strip 98 directly or, as shown in FIG. 6, through one or more spacer pads 86 and 92 which are preferably of different thicknesses to maximize the number of possible spacings. Spacer pad 86, also shown in FIG. 7, carriers complementary strips 88 and 90 of hook and pile material similar to that of strips 98 and 36, respectively. Spacer pad 92, which is similar to pad 86 but twice as thick, carries strips 94 and 96 similar to strips 88 and 90, respectively. If desired, there may also be interposed, between earcup 10 and helmet shell 84, the side panel (not shown) of an inner helmet suspension that is similarly provided with hook and pile fastener strips on its opposite surfaces. Such an arrangement is shown in Aileo U.S. Pat. Nos. 4,231,117 and 3,943,572, the disclosures of which are incorporated herein by reference. If the earcup assembly is intended soley for use in helmets such as helmet 84 having hook and pile fasteners, tabs 16 to 30 may be omitted.

Preferably, the external dimensions of earcup assembly 10 are identical to those of the earcup, such as shown in Aileo U.S. Pat. Nos. 3,470,564 or 3,875,592, that it is intended to replace. However, because the shell 12 is thinner, the internal dimensions of the shell will be greater.

It will be seen that we have accomplished the objects of our invention. Our earcup assembly minimizes the transmission of impact forces while at the same time satisfactorily attenuating ambient sounds. Our earcup assembly is relatively lightweight and conforms to the contours of a wearer's head. Our earcup assembly also operates satisfactorily in cold weather. Finally, our assembly in compatible with existing helmets.

It will be understood that certain features and subcombinations are of utility and may be employed without reference to other features and subcombinations. This is contemplated by and is within the scope of our claims. It is further obvious that various changes may be made in details within the scope of our claims without departing from the spirit of our invention. It is, therefore, to be understood that our invention is not to be limited to the specific details shown and described.

Having thus described our invention, what we claim is:

1. A sound attenuating earcup assembly for insulating the ear of a wearer from ambient sound while inhibiting the transmission to the wearer's head through the assembly of shocks of impact from severe bumps or he like which might otherwise injure the head of the wearer including in combination a discrete hollow rigid cup-shaped crushable shell forming a cavity for receiving the wearer's ear, said shell having a periphery, a seal extending around said periphery, means mounting said shell on the wearer's head for movement of said seal into engagement with the wearer's head around his ear and with the wall of the shell spaced from the wearer's ear to form a sound attenuating chamber around the ear, said shell being formed of such a material and of such a thickness as to maintain its rigidity in ordinary use and to collapse upon impact from such severe bumps or the like to dissipate energy at an applied force less than that required to crush the skull of the wearer and a layer of sound-deadening material on the inside of said shell.

2. An earcup assembly as in claim 1 in which said shell comprises a plastic.

3. An earcup assembly as in claim 1 in which said shell comprises an acrylonitrile-butadiene-styrene terpolymer.

4. An earcup assembly as in claim 1 in which said shell has a thickness of about 0.09 inch.

5. An earcup assembly as in claim 1 in which said layer is a coating of sound-deadening material permanently formed on the inside surface thereof.

6. An earcup assembly as in claim 1 including means forming a channel extending circumferentially along the outer surface of said shell, said channel-forming means comprising respective pluralities of circumferentially spaced outwardly extending tabs defining the sides of said channel.

7. An earcup assembly as in claim 1 including a compliant earseal for sealing the region between said shell and the wearer's head.

8. A helmet assembly including an earcup as in claim 1, a rigid helmet shell, and means for mounting said earcup assembly within said helmet shell.

9. An assembly as in claim 8 in which said mounting means comprises means supported by said helmet shell for forming an opening and means forming a channel extending circumferentially along the outer surface of said earcup shell for receiving the edges of said opening, said channel-forming means comprising respective pluralities of circumferentially spaced outwardly extending tabs defining the sides of said channel.

10. An earcup assembly as in claim 1 in which said sound-deadening layer comprises a rubber material.

11. An earcup assembly as in claim 1 in which said sound-deadening layer has a thickness of from about 0.010 to about 0.015 inch.

12. An earcup comprising a shell adapted to fit over a wearer's ear and means forming a channel extending circumferentially along the outer surface of said shell, said channel-forming means comprising respective pluralities of circumferentially spaced outwardly extending tabs defining the sides of said channel.

13. An earcup as in claim 12 in which said first and second pluralities of tabs are offset relative to each other.

14. An earcup as in claim 12 in which said first and second pluralities of tabs are nonoverlapping.

15. An earcup as in claim 12 in which said tabs are of reduced height at their ends.

16. An earcup as in claim 15 in which said tabs are rounded.

17. An assembly as in claim 1 in which said seal comprises a first layer of relatively slow-recovery impact absorbing material and a second layer of relatively quick recovery resilient material.

18. An assembly as in claim 17 in which said dissipative layer is relatively adjacent to said shell and said second layer is relatively adjacent to the wearer's head.

19. An assembly as in claim 17 in which said first layer material comprises a slow-recovery foam.

20. An earseal assembly as in claim 17 in which said materials comprise polyurethane foams.

21. An assembly as in claim 17 including means for securing said layers to said shell with said first layer relatively adjacent to said shell and said second layer relatively adjacent to the wearer's head.

22. An assembly as in claim 17 in which said first layer comprises a slow-recovery polyurethane foam and said second layer comprises a normal-recovery polyurethane foam.

23. An assembly as in claim 17 including an envelope encasing said material.

24. An assembly as in claim 23 in which said envelope has an annular lip adapted to be stretched over the periphery of said shell.

* * * * *

UNITED STATES PATENT AND TRADEMARK OFFICE
CERTIFICATE OF CORRECTION

PATENT NO. : 4,905,322

DATED : March 6, 1990

INVENTOR(S) : Jackson A. Aileo and Richard J. Long

It is certified that error appears in the above-identified patent and that said Letters Patent is hereby corrected as shown below:

Column 5, line 58 - delete " he ", insert -- the --.

Column 6, line 25 - after " earcup", insert -- assembly --.

Column 6, lines 60 and 61 - delete " dissipative ", insert -- first --.

Column 6, line 65 - delete " earseal ".

Signed and Sealed this

Twenty-sixth Day of February, 1991

Attest:

HARRY F. MANBECK, JR.

*Attesting Officer*   *Commissioner of Patents and Trademarks*